United States Patent [19]
Plog et al.

[11] Patent Number: 6,069,013
[45] Date of Patent: May 30, 2000

[54] SENSOR FOR THE SELECTIVE DETECTION OF AMMONIA IN $NO_x$-CONTAINING, OXYGEN-RICH GASES

[75] Inventors: Carsten Plog; Werner Maunz, both of Markdoff; Ralf Mueller, Aulendorf, all of Germany

[73] Assignee: DORNIER GmbH, Germany

[21] Appl. No.: 09/016,946

[22] Filed: Feb. 2, 1998

[30] Foreign Application Priority Data

Feb. 1, 1997 [DE] Germany .......................... 197 03 796

[51] Int. Cl.[7] .................................................. G01N 27/12
[52] U.S. Cl. .............................................. 436/113; 422/98
[58] Field of Search .................................. 436/113, 106, 436/149; 422/83, 98

[56] References Cited

U.S. PATENT DOCUMENTS

| | | | |
|---|---|---|---|
| 4,894,142 | 1/1990 | Steigleder | 208/111 |
| 4,929,581 | 5/1990 | Steinwandel et al. | 502/2 |
| 5,143,696 | 9/1992 | Haas et al. | 422/90 |
| 5,782,087 | 7/1998 | Kinugasa et al. | 60/276 |
| 5,879,631 | 3/1999 | Wewers et al. | 422/98 |

*Primary Examiner*—Jill Warden
*Attorney, Agent, or Firm*—Evenson, McKeown, Edwards & Lenahan, P.L.L.C.

[57] ABSTRACT

A sensor for selective detection of ammonia in high-oxygen, $NO_x$-containing gas. The sensor has a component part acting as the capacitor, and a gas-permeable sensitive layer as the dielectric, the sensitive layer being a hydrophobic, precious-metal-free zeolite of low acidity which has an ordered crystalline structure of primary-pores whose diameter is of the magnitude of the gas-kinetic diameter of $NH_3$.

18 Claims, 8 Drawing Sheets

SENSOR FOR THE SELECTIVE DETECTION OF AMMONIA IN $NO_x$-CONTAINING, OXYGEN-RICH GASES

BACKGROUND AND SUMMARY OF THE INVENTION

This application claims the priority of Germany Application No. 197 03 796.8, the disclosure of which is expressly incorporated by reference herein.

The invention relates to a sensor for selective detection of ammonia ($NH_3$) in $NO_x$-containing high-oxygen gases. Such gases include exhaust gases of diesel engines, exhaust gases of injected Otto engines or the exhaust of a power plant.

It is known that nitrogen removal from diesel engine exhaust gases can be carried out by selective catalytic reduction (SCR) using ammonia as a reducing agent. Ammonia can be carried in vehicles either directly or in a compound.

For the catalytic reaction, ammonia is metered to engine exhaust gas at a fixed ratio to $NO_x$. The $NH_3$—$NO_x$ ratio for achieving maximally possible $NO_x$-conversion would have to be exactly 1. A smaller ratio leads to a smaller conversion; a larger ratio leads to an "$NH_3$ breakthrough". Since neither $NO_x$ sensors nor $NH_3$ sensors suitable for the vehicle are available, $NO_x$ values are obtained from characteristic engine diagrams stored in a computer.

$NH_3$ emission must be securely prevented in all operating conditions. However, characteristic $NO_x$ diagrams do not apply to individual engines, but to a line of products, so that fluctuations in $NO_x$ crude gas content occur caused by manufacturing, while characteristic engine diagram points are the same. In addition, a momentary catalyst condition (temperature, $NO_x$ and $NH_3$ charge) may be different while characteristic diagram points are the same. Accordingly, an $NH_3/NO_x$ ratio is selected in practice which is clearly smaller than 1, (for example, 0.6) so that a sufficiently large safety margin can be maintained. Thus, poorer nitrogen oxides removal is intentionally accepted.

In order to achieve $NO_x$ limit values, NO crude engine emission must be reduced further than necessary. With respect to diesel engines, this reduces efficiency.

A better use of a nitrogen oxide removal catalyst could be achieved with an $NH_3$ sensor. Such a sensor could be mounted as a control element or as an $NH_3$ breakthrough sensor. Under diesel engine exhaust gas conditions, the $NH_3$ sensor would have to detect a small amount of $NH_3$ in a secure manner without any significant cross sensitivity to other relevant gases (mainly $NO_x$, $H_2O$ and $O_2$).

European Patent Document EP 0426 989 B1 describes a chemical sensor for gases on the basis of zeolite-coated, directly heated, planar interdigital capacitors (in the following abbreviated as "IDK"). In one embodiment, this sensor consists of a platinum-containing zeolitic layer.

Figure 1:
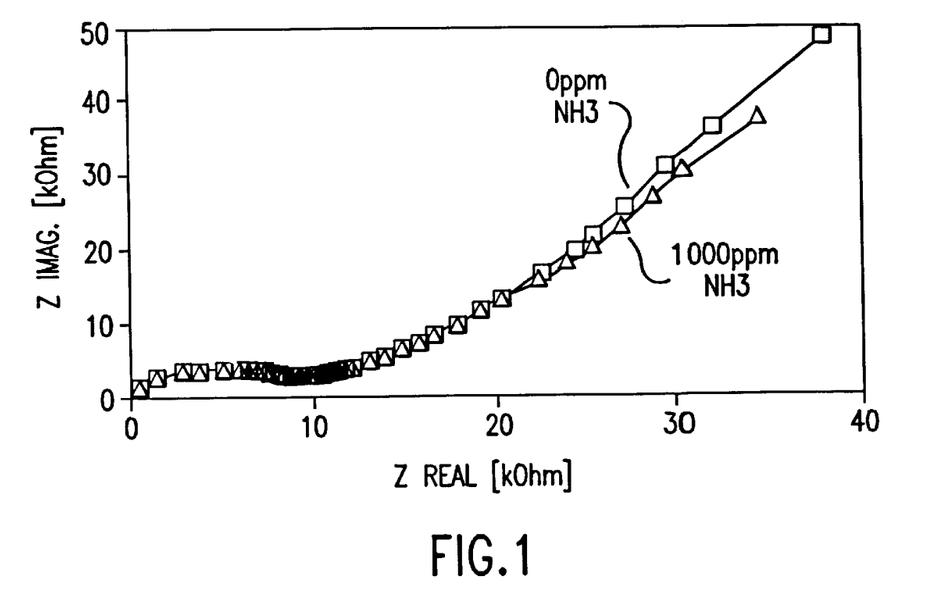
FIG. 1 is a representation of impedance spectra of an IDK sensor of the prior art coated with PtZSM5 and acted upon by 1,000 ppm NH₃ (triangular symbols) and 0 pp NH₃ (rectangular symbols)
Figure 2A:
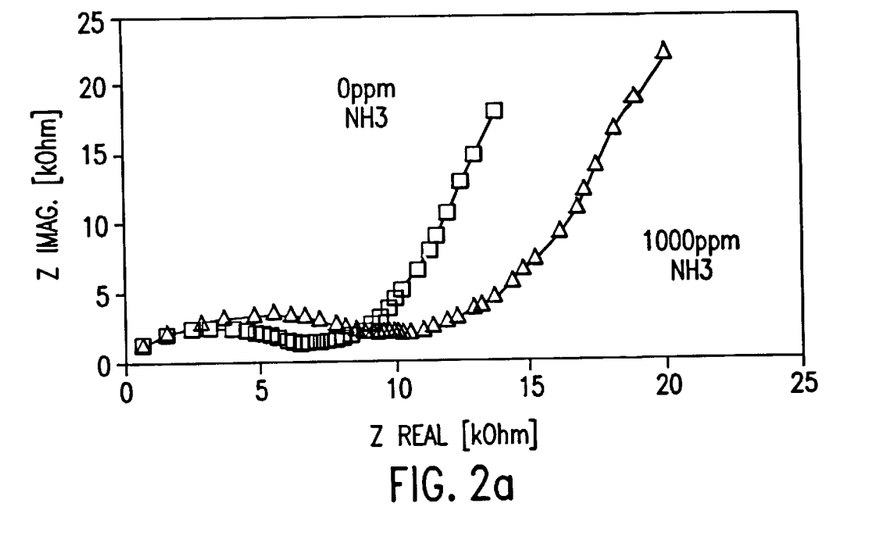
FIG. 2a is a representation of impedance spectra of an IDK sensor of the prior art coated with a PtY zeolite acted on by 1,000 ppm NH₃ (triangular symbols) and 0 ppm NH₃ (rectangular symbols)
Figure 2B:
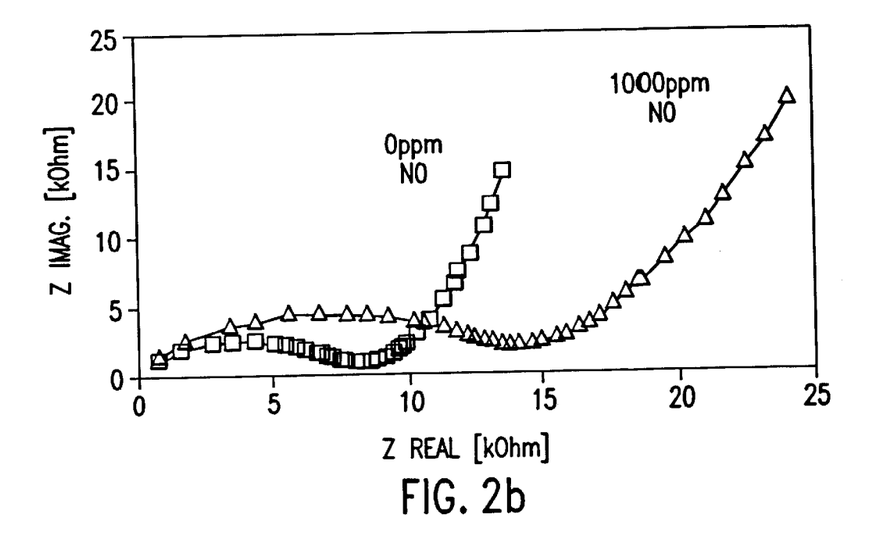
FIG. 2b shows the impedance spectra of this IDK sensor with and without NO.

During the investigations concerning $NH_3$ sensitivity, it was found that IDK sensors which are coated with precious-metal-containing zeolites cannot be used as $NH_3$ sensors in exhaust gas for two reasons: either they lack sufficiently high $NH_3$ sensitivity (FIG. 1), or they have $NH_3$ sensitivity, (FIG. 2a) but simultaneously have a very high cross sensitivity to NO (FIG. 2b).

FIG. 1 is a representation of impedance spectra (frequency range: 20 Hz to 1 MHz) of an IDK sensor of the prior art, which is coated with PtZSM5 and acted upon by 1,000 ppm $NH_3$ (triangular it symbols) and 0 ppm $NH_3$ (rectangular symbols) in 10% $O_2$, 5% abs $H_2O$, with "abs" representing percent by volume.

FIGS. 2a and 2b are representations of impedance spectra of an IDK sensor of the prior art, which is coated with a PtY zeolite and in 10% $O_2$, 5% abs $H_2O$; FIG. 2a: at 1,000 ppm $NH_3$ (triangular symbols) and 0 ppm $NH_3$ (rectangular symbols); FIG. 2b: at 1,000 ppm NO (triangular symbols) and 0 ppm NO rectangular symbols). FIG. 2b shows the impedance spectra of this IDK sensor with and without NO. Here, it is found that this type of sensor is also sensitive to NO. This cross sensitivity to NO does not permit a use as an $NH_3$ sensor in exhaust gas.

It is an object of the invention to provide a sensor which detects small amounts of $NH_3$ in a secure manner and without any significant cross sensitivity to other relevant gases (mainly $NO_x$, $H_2O$ and $O_2$).

This object is achieved according to the invention with an $NH_3$ sensor comprising a component part acting as a capacitor and a gas-permeable sensitive layer as the dielectric, the sensitive layer being a hydrophobic, precious-metal-free zeolite of a low acidity (acidic strength) which has an ordered crystalline structure of primary pores whose diameter is in the order of the gas-kinetic diameter of $NH_3$.

The interaction of the molecule to be detected with the precious-metal-free zeolitic solid state sensor according to the invention takes place completely differently than in the case of the sensor described in European Patent Document EP 0 426 989 B1. In the case of the platinum-containing zeolitic layer, a catalytic conversion of the gas molecules takes place at the platinum clusters within the zeolitic pore system. By means of the reaction, which does not take place infinitely fast with respect to time, the mobility of the cations (generally sodium ions) of the zeolite, is hindered, but they can be moved at a raised temperature through the electric alternating field. The reduction of the mobility of cations becomes noticeable at low frequencies as a change of impedance.

In the case of sensors according to the invention having a precious-metal-free hydrophobic zeolite layer as the ammonia-sensitive layer, no catalytic conversion of the $NH_3$ takes place, because the eligible zeolites have no catalytic conversion activity for $NH_3$. In contrast, the adsorption of the ammonia molecule plays a determining role with respect to the behavior of the sensor. The protons of the adsorbed ammonia molecules are the charge carriers whose mobility in the electric alternating field generates the sensor signal. Ionic conductivity changes in the whole examined frequency range from 20 Hz to 1 MHz. At the high frequencies, only the protons can still follow the alternating field; the much heavier other eligible cations can no longer do so.

The hydrophobic character of the zeolites is determined by their tendency to absorb polar molecules (such as water) only in very low quantities, but homopolar compounds (such as hydrocarbons) in large quantities. Since, during the generating of the signal of the $NH_3$ sensor according to the invention, the adsorption condition of the $NH_3$ molecule in the zeolitic pore system plays the decisive role, it is important that only a small quantity of water is present in the pore system. On the one hand, the $NH_3$ could dissolve in the pore water as ammonium hydroxide ($NH_4OH$) and could partially dissociate. On the other hand, the cross sensitivity to the water would be too high.

Other objects, advantages and novel features of the present invention will become apparent from the following detailed description of the invention when considered in conjunction with the accompanying drawings.

DETAILED DESCRIPTION OF THE PREFERRED EMBODIMENTS

Extensive investigations of the NH₃ sensitivity of zeolitic IDK sensors were carried out as a function of the used zeolite type and of the used zeolite modification. NH₃ sensor sensitivity as well as cross sensitivity to NO, H₂O, CO, HC were investigated. Zeolites were used in the Na-form and in the H-form. These cations were carried out by other elements by the ion exchange of cationic compounds of these elements.

FIG. 1 shows the impedance spectra (frequency range: 20 Hz to 1 MHz) of a prior art IDK sensor with a PtNaZSM5-layer with (triangular symbols) and without (rectangular symbols) NH₃. In the whole frequency range, the difference between the impedance spectrum with 1,000 ppm NH₃ and 0 ppm NH₃ is very low: this sensor shows no NH₃ sensitivity.

FIG. 2a shows the impedance spectra of a prior art IDK sensor with a PtNaY layer with (triangular symbols) and without (rectangular symbols) NH₃. The impedance spectrum with 1,000 ppm, in comparison to that at 0 ppm NH₃, is clearly displaced toward lower frequencies. This type of sensor is sensitive to NH₃, yet also sensitive to NO$_x$.

Figure 3A:
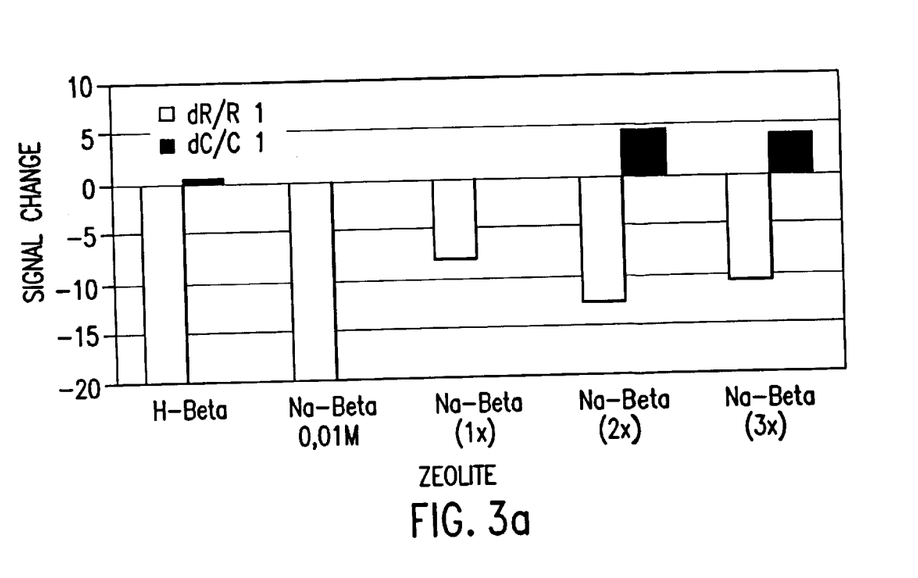
FIG. 3a is a graphical representation of relative resistance changes dR/R1 (white bars) and relative capacitance changes dC/C1 (dark bars) for different modifications of the zeolite type Beta in the case of an NH₃ concentration change.
Figure 3B:
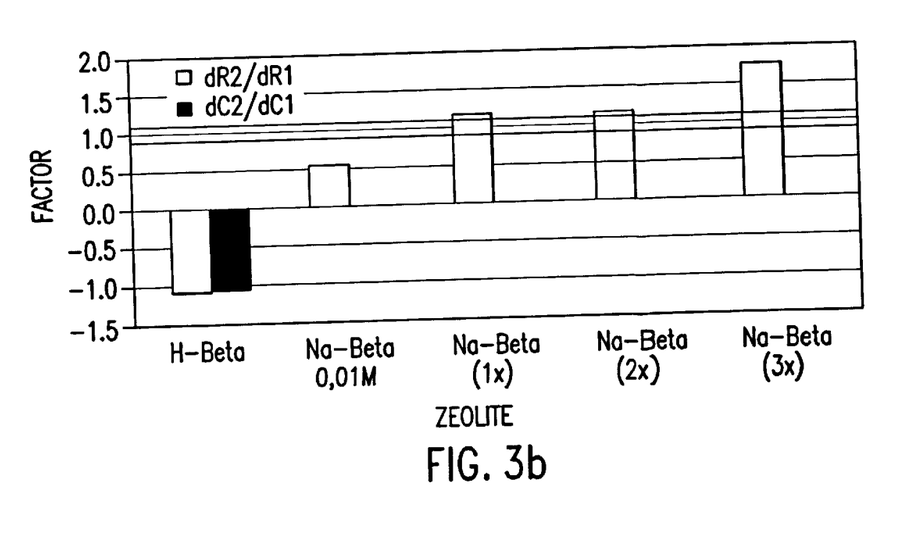
FIG. 3b is a graphical representation of the resistance change dR2 (white bars) and the capacitance change dC2 (dark bars) in the case of an NO concentration change in comparison to the resistance or capacitance change dR1 or dC1 in the case of an NH₃ concentration change.

FIG. 3a shows NH₃ sensor sensitivity and NO cross sensitivity in FIG. 3b for modifications of the Beta zeolite.

Figure 4A:
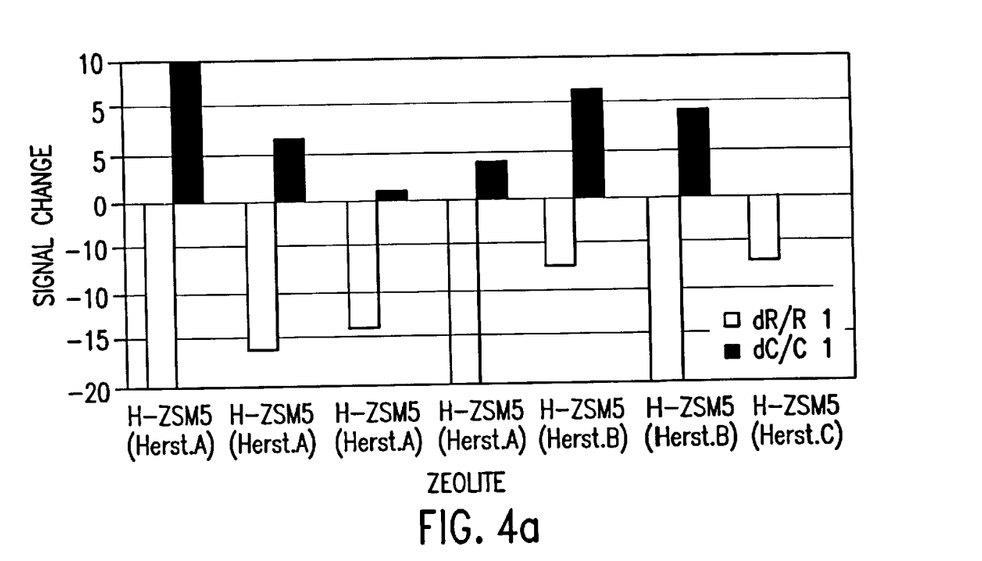
FIG. 4a is a representation of relative resistance changes dR/R1 (white bars) and relative capacitance changes dC/C1 (dark bars) for different moduli of the zeolite type ZSM5 in the case of an NH₃ concentration change.
Figure 4B:
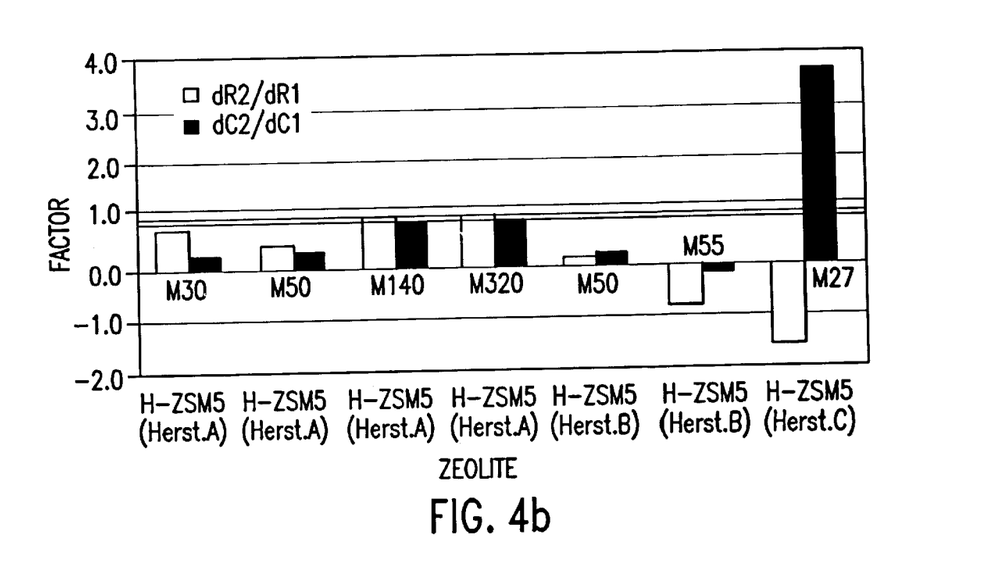
FIG. 4b is a representation of the resistance change dR2 (white bars) and the capacitance changes dC2 (dark bars) in the case of an NO concentration change in comparison to the resistance or capacitance change dR1 or dC1 in the case of an NH₃ concentration change.

In all illustrated modifications, the modulus is essentially the same. FIG. 4a illustrates NH₃ sensor sensitivity and NO cross sensitivity at FIG. 4b for different moduli of zeolite type ZSM5 in the H-form. Zeolites of different manufacturers were taken into account. Both were at 10% O₂, 5% abs H₂O, 251 ppm NO; In FIG. 4, the manufacturers are called "Manufacturer A", "Manufacturer B", Manufacturer C".

With respect to diagrams concerning NO cross sensitivity, it should be taken into account that, in the case of the factor 1.0, there is no NO influence. The measuring columns of suitable sensor materials therefore end in the drawn interval about the factor 1.0.

The measurements were carried out at 10% O₂ and 5% abs H₂O such that (1) NH₃ was increased from 0 to 124 ppm, in which case, 251 ppm NO was in the measuring gas, (2) NO was increased from 251 ppm to 653 ppm, in which case 124 ppm NH₃ was in the measuring gas.

By means of this measuring procedure, the actual NO/NH₃ concentrations were taken into account which were present in the case of a defined NO$_x$ crude emission after a specific catalyst length (30% of the overall length) at a certain NO conversion (60%).

FIGS. 3a and 3b show the result which had not been known: NH₃ sensitivity and NO cross sensitivity can be influenced in the case of the same zeolite type (in the example "Beta") by the type and concentration of exchange cations and thus by the acidity of the modified zeolite.

FIGS. 4a and 4b show the result which had not been known: NH₃ sensitivity and NO cross sensitivity in the case of the same zeolite form (in the example "H-form") depends on the selection of the modulus and thus the acidity of the zeolite.

Surprisingly, this provides the possibility of adjusting the cross sensivity with respect to NO by the exchange of different proportions of cations, by the type of the cation, by the selection of the zeolite type and by the modulus of the zeolite and therefore by the adjusting of the acidity of the zeolites.

Thus, the H-Beta condition with a resistance reduction of 72% is very sensitive to NH₃, but simultaneously also very cross sensitive to NO. The reason is that, by means of an NO concentration change from 251 to 653 ppm, the resistance will change by a factor of −1.1. This means that the resistance increases again and reaches its starting value of the NH₃-admission. In FIG. 3, the specimens Na Beta (0.01 M), Na Beta (1×), Na Beta (2×) and Na Beta (3×) represent an increasing sodium ion concentration, whereby the acidity is reduced. The zeolites Na Beta (1×) and Na Beta (2×) exhibit almost no NO cross sensivity (factor 1.0 means that there is no NO influence).

FIGS. 4a and 4b show several zeolites of the ZSM5 type, in which case the modulus of the individual zeolites of the same manufacturer becomes smaller from the left to the right, whereby the acidity is reduced. This figure illustrates that, for example, an H-ZSM5 with a modulus of 140 is sensitive with respect to $NH_3$ but not cross sensitive with respect to NO, while an HZSM5 of the same manufacturer with a modulus of 50 is very $NH_3$-sensitive but simultaneously also has a high NO cross sensitivity.

Figure 5:
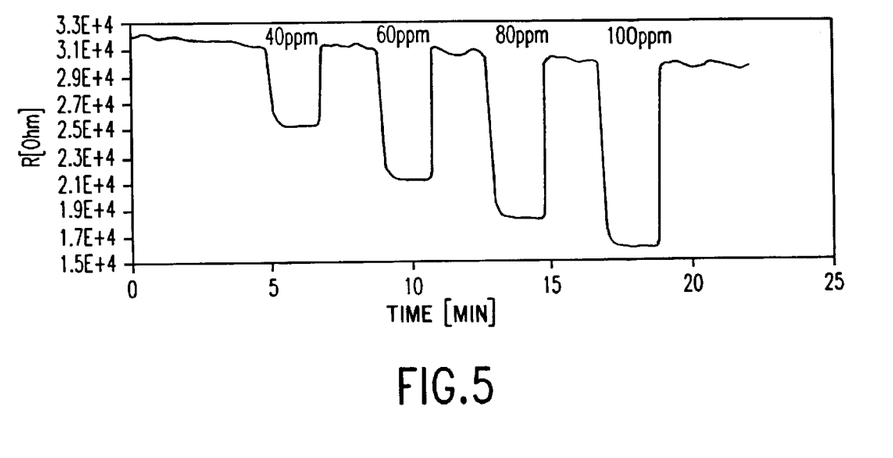
FIG. 5 is a representation of resistance changes over time for the zeolite type H-ZSM5 by different NH₃ concentrations.

FIG. 5 exhibits $NH_3$ sensitivity for the H-ZSMF zeolite type (modulus 140) as an embodiment of the $NH_3$ sensor according to the invention. The sensor is successively acted upon by 40 ppm, 60 ppm, 80 ppm, 100 ppm $NH_3$ in a measuring gas with 1,000 ppm NO, 5% abs $H_2O$ and 10% $O_2$; the sensor operating temperature was 420° C., and the measuring gas temperature 260° C. As the result of 40 ppm $NH_3$, the resistance decreases from 31 to 25 kOhm. This corresponds to a 20% reduction of the resistance. At 100 ppm $NH_3$, the resistance falls by half to 15 kOhm.

Figure 6:
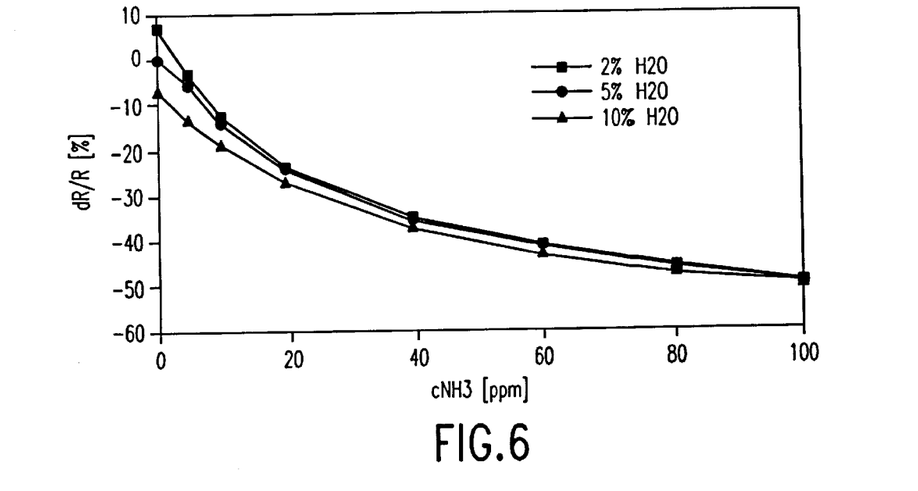
FIG. 6 is a representation of relative resistance changes dR/R for the zeolite type H-ZSM5 by different NH₃ concentrations.

For different $H_2O$ concentrations (2%, 5%, 10%) in the feed gas, FIG. 6 shows the dependence between the resistance reduction and the $NH_3$ concentration of an H-ZSM5 zeolite according to the invention with the modulus 140 in a measuring gas with 10% $O_2$, 2% $H_2O$ (square), 5% $H_2O$ (rhombus), 10% $H_2O$ (triangle); the sensor operating temperature was 420° C., and the measuring gas temperature 260° C. Only in the case of very low $NH_3$ concentrations can a change of $H_2O$ concentrations have a disturbing effect in the relative value range. Starting at 40 ppm $NH_3$, this residual cross sensitivity with respect to water is no longer important.

Figure 7:
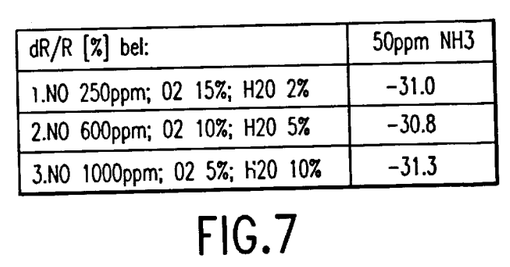
FIG. 7 is a representation of relative resistance changes dR/R for the zeolite type H-ZSM5 by different concentrations of NO, O₂ and H₂O but constant NH₃-gas pulse.

In a table form, FIG. 7 shows the signal change of an $NH_3$ sensor according to the invention (H-ZSM5, modulus 140) which, in the case of different feed-gas-compositions, is caused by 50 ppm $NH_3$. The feed gas compositions correspond to the conditions during idling and intermediate load and full load after a certain length of an SCR catalyst with a defined $NO_x$ conversion at 50 ppm at different operating points: 1. idling, 2. medium load, 3. full load; the sensor operating temperature was 420° C., and the measuring gas temperature was 260° C. It is found that 50 ppm $NH_3$ can be reliably recognized in all load conditions independently of the respective content of NO, $O_2$ and $H_2O$.

Figure 8:
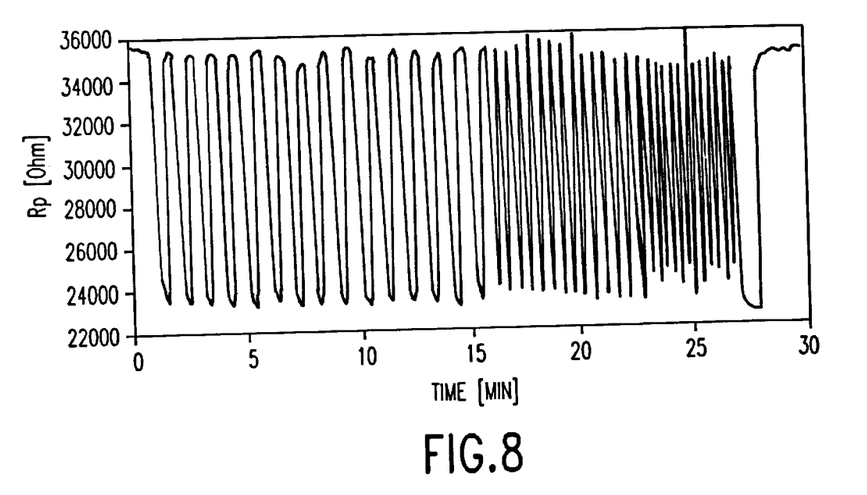
FIG. 8 is a representation of resistance changes for the zeolite type H-ZSM5 with diffrent NH₃ concentratation changes between 0 ppm and 50 ppm NH₃.

FIG. 8 shows the response characteristics of an $NH_3$ sensor according to the invention by means of the resistance change on the basis of periodic $NH_3$ concentration changes between 0 and 60 ppm in a measuring gas with 10% $O_2$, 5% $H_2O$; the sensor operating temperature was 420° C., the measuring gas temperature was 260° C. The gas admission was carried out as follows:

0–16 min: 30 sec 60 ppm $NH_3$, 30 sec 0 ppm $NH_3$
16–23 min: 20 sec 60 ppm $NH_3$, 20 sec 0 ppm $NH_3$
23–27 min: 15 sec 60 ppm $NH_3$, 15 sec 0 ppm $NH_3$ In this embodiment, the $NH_3$ sensor has a T50 response characteristic in the range of 2 sec.

Figure 9A:
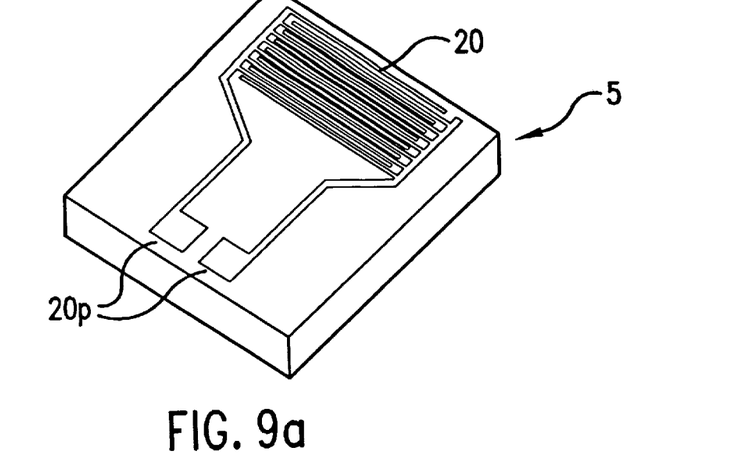
FIG. 9a is a top view of the sensor according to the invention.
Figure 9B:
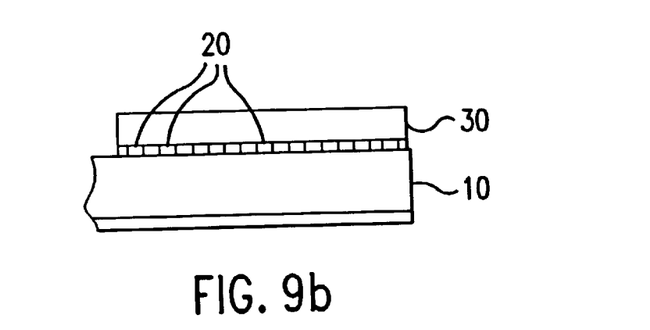
FIG. 9b is a sectional view of the sensor according to the invention.
Figure 9C:
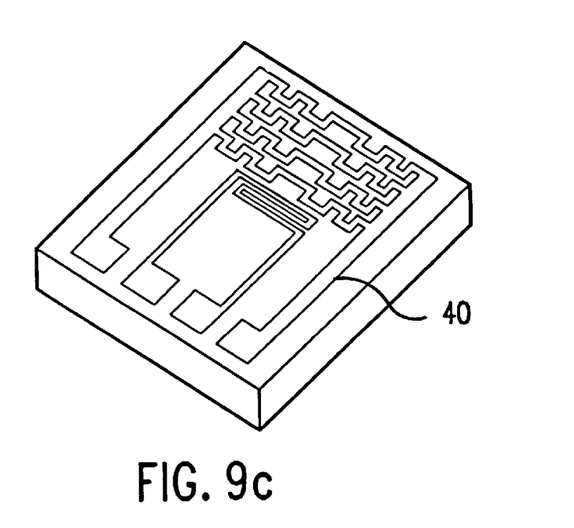
FIG. 9c is a top view of the sensor according to the invention.

FIGS. 9a–9c schematically show a sensor S according to the invention with an interdigital capacitor 20 as the component part acting as the capacitor as well as a gas-permeable sensitive zeolite layer 30. FIG. 9a is a top view of the sensor. FIG. 9b is a sectional view of the sensor. FIG. 9c is a bottom view of the sensor, in which the heater structure 40 is visible.

The parallel strip conductors (for example, made of Au) of the interdigital capacitor 20 are applied to a substrate 10, for example, of quartz glass, Si or $Al_2O_3$. These parallel strip conductors are wired such that an arrangement of capacitors is obtained which are electrically connected in parallel, a single capacitor in each case comprising two adjacent strip conductors. The conductors forming the capacitor 20 are connected in use via contact pads 20P to control circuitry connected with a computer control unit. Above and between the strip conductors of the capacitor 20, the gas-permeable sensitive zeolite layer 30 is arranged. The layer thickness of the zeolite layer 30 is, for example, in the order of 40 µm. On the underside of the substrate 10, a heater 40 is arranged whose structure, consisting of individual heater wires, is schematically shown in FIG. 9C.

Figure 10:
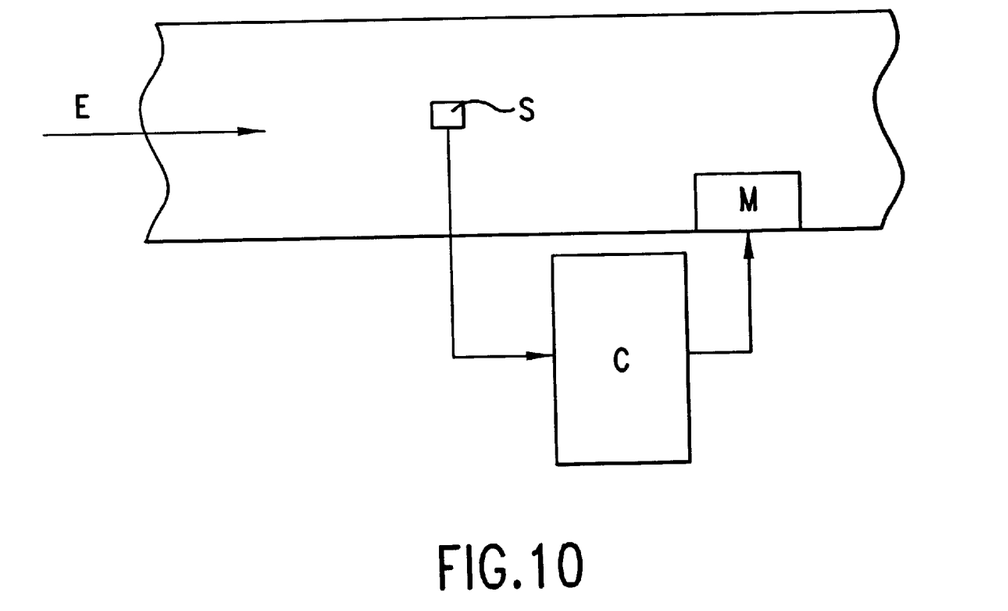
FIG. 10 is a sample circuit including the sensor.

FIG. 10 schematically depicts a configuration utilizing the sensor S according to the present invention. This sensor S is placed into a position where it can detect the exhaust gas flowing through an exhaust line E. Output signals from the sensor S are fed to a computer control unit C, which then utilizes this sensed information to control a Meter M for metering supply of $NH_3$ or the like as a reducing agent.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A sensor for selective detection of ammonia in oxygen-rich, $NO_x$-containing gas which comprises
   (a) a component part acting as a capacitor and
   (b) gas-permeable sensitive layer as a dielectric, the sensitive layer being a hydrophobic precious-metal-free zeolite of low acidity which has an ordered crystalline structure of primary pores whose diameter is of the magnitude of the gas-kinetic diameter of $NH_3$.

2. A sensor according to claim 1, wherein the acidity of the sensitive layer is adjusted by exchange of different proportions of cations, by the type of cation, by selection of the zeolite type or by a modulus of the zeolite.

3. A sensor according to claim 1, wherein the oxygen concentration is between 20% and 5,000 ppm.

4. A sensor according to claim 1, wherein the zeolite is a Y—, USY, mordinite, ZSM5, ZSM 12, Beta, L, SAPO-11, SAPO-34 or MCM41.

5. A sensor according to claim 4, wherein the zeolite is present in the pure H-form or the pure Na-form, or is partially or completely exchanged with alkali metals, alkaline earth metals or transition elements.

6. A sensor according to claim 4, wherein a lattice $Al^+$ of the zeolite is partially replaced by transition elements.

7. A sensor according to claim 4, wherein the oxygen-rich $NO_x$-containing gas is the exhaust gas of a diesel engine or of a lean operating Otto engine.

8. A sensor according to claim 1, wherein the oxygen-rich $NO_x$-containing gas is the outgoing air of a power plant.

9. A sensor according to claim 1, wherein the component acting as the capacitor is an interdigital capacitor.

10. A method for the selective detection of ammonia in oxygen-rich, $NO_x$-containing gas, comprising:
   exposing the gas to a sensor comprising
      (a) a component part acting as a capacitor and
      (b) a gas-permeable sensitive layer as a dielectric, the sensitive layer being a hydrophobic precious-metal-free zeolite of low acidity which has an ordered crystalline structure of primary pores whose diameter is of the magnitude of the gas-kinetic diameter of $NH_3$;
   measuring a change in resistance of the sensor; and
   correlating the change to a concentration of ammonia in the gas.

11. The method according to claim 10, wherein the acidity of the sensitive layer is adjusted by exchange of different proportions of cations, by the type of cation, by selection of the zeolite type or by a modulus of the zeolite.

12. The method according to claim 10, wherein the oxygen concentration is between 20% and 5,000 ppm.

13. The method according to claim 10, wherein the zeolite is a Y—, USY, mordinite, ZSM5, ZSM 12, Beta, L, SAPO-11, SAPO-34 or MCM41.

14. The method according to claim 13, wherein the zeolite is present in the pure H-form or the pure Na-form, or is partially or completely exchanged with alkali metals, alkaline earth metals or transition elements.

15. The method according to claim 13, wherein a lattice $Al^+$ of the zeolite is partially replaced by transition elements.

16. The method according to claim 13, wherein the oxygen-rich $NO_x$-containing gas is the exhaust gas of a diesel engine or of a directly injecting Otto engine.

17. The method according to claim 10, wherein the oxygen-rich $NO_x$-containing gas is the outgoing air of a power plant.

18. The method according to claim 10 wherein, the component acting as the capacitor is an interdigital capacitor.

* * * * *